United States Patent [19]

Stautzenberger

[11] Patent Number: 4,767,881

[45] Date of Patent: Aug. 30, 1988

[54] SYNTHESIS OF DIPHENYL PHTHLATES

[75] Inventor: A. Lee Stautzenberger, Nueces, Tex. 78411

[73] Assignee: Hoechst Celanese Corporation, Chatham, N.J.

[21] Appl. No.: 72,314

[22] Filed: Jul. 13, 1987

[51] Int. Cl.$^4$ .............................................. C07C 67/08
[52] U.S. Cl. ..................................... 560/86; 502/171; 560/99
[58] Field of Search ..................... 560/86, 99; 502/171

[56] References Cited

U.S. PATENT DOCUMENTS 3,076,837 2/1963 Mills ...................................... 560/86

Primary Examiner—Werren B. Lone
Assistant Examiner—Vera C. Clarke
Attorney, Agent, or Firm—Depaoli & O'Brien

[57] ABSTRACT

Diphenyl esters of aromatic carboxylic acids are prepared in the presence of an organozirconium catalyst.

5 Claims, No Drawings

SYNTHESIS OF DIPHENYL PHTHLATES

BACKGROUND OF THE INVENTION

1. Field of the Invention

The present invention relates to the preparation of phenolic esters of aromatic carboxylic acids and more particularly to the preparation of diphenyl esters of aromatic carboxylic acids, such as phthalic acid, to provide ester monomer products having good color properties.

2. Description of the Prior Art

The production of various phenolic esters of aromatic benzenedicarboxylic acids, such as diphenyl terephthalate and monophenyl terephthalate, has become of significant commercial interest in recent years due to their use in a great many types of processes. As an example, diphenyl terephthalate and diphenyl isophthalate when dissolved in a solvent may be reacted with a primary diamine to produce polyamides. Likewise, 3,3'-diaminobenzidine may be condensed with various diphenyl esters to form polybenzimidazoles. In the synthesis of commercial resins, such as Durel ®, diphenyl phthalates are reacted with bisphenol A to provide polyarylate resins which find extensive commercial use. The diphenyl phthalate esters may be produced by reaction of acid chlorides with a phenol to produce the phenyl ester and hydrogen chloride as a by-product, or by reacting a phenolic compound and aromatic dicarboxylic acid in the presence of a catalyst consisting of an alkali metal compound and boron compound. Other methods of preparation include catalyzing the reaction of phenol and phthalic acid with strong acids, such as alkylsulfonic acid, or with organotitanate catalysts such as titanium-n-butoxide. While such processes are effective for producing phenolic esters they suffer the disadvantage that during the process of esterification, the ester acquires a pink to dark brown color which methods of purification such as vacuum distillation, recrystallization and/or carbon treatment, are insufficient to remove. With organotitanate catalysts, for example, the titanates form extremely colored complexes with phenoxy moieties which appear to contribute to the dark color of the recovered diphenyl phthalate and which are carried through when production of polyarylate resins. According, there is a need the monomer is subsequently reacted with bisphenol A in the for additional preparational methods that can produce specification grade diphenyl phthalates having good quality color properties.

U.S. Pat. No. 2,720,504 discloses preparation of polyesters in the presence of catalyts which are alkali metal and alkaline earth metal salts containing a complex zirconium hexalkoxide radical. U.S. Pat. No. 2,930,785 discloses a process for polymerizing olefins in the presence of a catalyst composition comprising a zirconium derivative, such as zirconium propionate and zirconium butoxide. U.S. Pat. No. 3,056,818 discloses a method for preparing esters in the presence of an organotitanium or organozirconium catalyst in which the organic group can be an alkoxyl group, such as butoxy titanium hexanoate by reacting aromatic acids, such as isophthalic and terephthalic acids, with alcohols such as phenylethanol. U.S. Pat. No. 3,927,052 discloses a polymerization catalyst prepared by reacting an organosilicon compound with an organozirconium compound to prepare glycol-dimethyl terephthalate polyesters. U.S. Pat. No. 4,241,216 discloses the preparation of phthalate diesters in the presence of lower alkyl zirconium esters. U.S. Pat. No. 4,444,904 relates to a process for preparing zirconium hydrocarboxide catalyst compositions such as tetraisopropoxide and tetra-n-propoxide. U.S. Pat. No. 4,440,946 discloses a reduced silver-cadmium-zinc-zirconium catalyst for producing carboxylate esters.

SUMMARY OF THE INVENTION

The present invention is directed to an improvement in the preparation of phenolic esters of aromatic carboxylic acids, especially the diphenyl esters, by catalyzing the preparation of such compounds with an organozirconium catalyst.

DESCRIPTION OF THE INVENTION

The organozirconium catalysts useful in this invention are zirconium alkoxides which are known compounds and which may be prepared, for example, by reaction of zirconium tetrahalides and alcohols or by reaction of zirconium dialkylamines with alcohols. In normal ester synthesis, catalysts such as organotitanates or Bronsted acids are preferably used because of their high reaction rates. In the synthesis of high molecular weight diphenyl esters of aromatic carboxylic acids, however, the use of zirconium alkoxides will form esters at a lower reaction rate than the titanates, but they produce esters which are less colored. Accordingly, in the preparation of diphenyl phthalate monomers according to the invention, the reaction rate is secondary to producing esters of high purity which do not contain colorizing materials.

Suitable organozirconium catalysts which may be used in this invention are zirconium alkoxides which contain 1 to 4 carbon atoms in the alkyl groups and include zirconium tetra-n-methoxide, zirconium tetra-n-ethoxide, zirconium tetra-n-propoxide, zirconium tetra-i-propoxide, and zirconium tetra-n-butoxide. The amount of catalyst employed will range from about 0.01 to 3.0 mol %, preferably .03 to 0.3 mol %, based on the aromatic carboxylic acids.

The esters are derived from aromatic carboxylic acids which should be essentially free of aldehydic and ketonic carbonyl groups as these groups interfere with the esterification reaction. Other than these aldo and keto groups, the aromatic carboxylic acid may contain various functional groups which will not interfere with the esterification reaction. Generally the aromatic carboxylic acid will contain no functional groups or radicals other than carboxyl, carboxylic ester, ether, thioether, aromatic ring-substituted halo, sulfo, or sulfonyl. The aromatic carboxylic acids which are free of ketonic and aldehydic carbonyl groups have the formula:

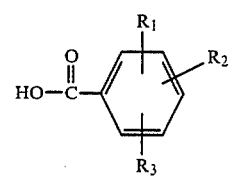

wherein $R_1$ and $R_2$ are alike or different and correspond to hydrogen, carboxyl or hydroxyl and wherein $R_3$ is hydrogen or an organic radical of six to 20 carbon atoms containing an aromatic ring, which organic radical is composed only of elements selected from the groups consisting of carbon, hydrogen, and oxygen.

Especially preferred are those dicarboxylic acids of the formula

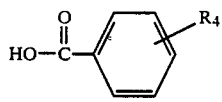

where $R_4$ is carboxyl group or a radical of seven to 20 carbon atoms of the formula

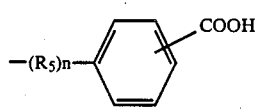

wherein n is 0 or 1 and $R_5$ is a divalent hydrocarbon radical, oxygen, or a divalent radical composed of carbon, hydrogen, and oxygen wherein the oxygen present is as an ether linkage. Among the acids containing aromatic ring-substituted carboxyl groups that may be esterified in accordance with the present invention are benzoic acid, phthalic acid, terephthalic acid, isophthalic acid, diphenic acid, homophthalic acid, toluic acid, alpha-naphthoic acid, chlorobenzoic acid, salicylic acid, 1,2-(ethylenedioxy)dibenzoic acid, and 2,5-dimethylterephthalic acid. Mixtures (3/1) of iso- and terephthalic acid are especially preferred.

The phenols utilized for production of an ester are mono functional phenols which contain only one phenolic hydroxyl group. Generally these phenols will be those of six to 15 carbon atoms of the formula

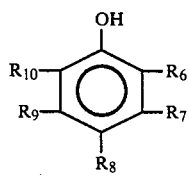

wherein $R_6$, $R_7$, $R_8$, $R_9$ and $R_{10}$ may be hydrogen, alkyl, alkaryl, aryl, or aralkyl radicals. Among the particular phenols that may be utilized are phenol, o-cresol, m-cresol, p-cresol, xylenols, either mixed or the pure isomer, o-phenylphenol, and p-phenylphenol. Of the various phenols that may be utilized, phenol itself is preferred over the others.

The reaction of the aromatic carboxylic acid with phenol in the presence of the organozirconium catalyst is carried out in the liquid phase in a customary manner using equipment normally used for esterification reactions. The organic carboxylic acid is reacted with an excess of the phenol, usually a three to fourfold excess, based on the amount of dicarboxylic acid, in order to form a solution of the ester in the phenol after completion of the esterification reaction. The reaction conditions can be varied depending upon the type of esters being formed and the particular phenol being employed. Solvents such as m-xylene can be used and a temperature sufficient to effect esterification in the presence of the organozirconium catalyst will be used. Generally the temperature will range from 220° C. to 290° C. under pressure or suitable reflux conditions. The water formed in the reaction may be stripped off as the phenol azeotrope or by other suitable azeotroping agents such as toluene or a xylene.

By using the above aromatic carboxylic acids and phenols and catalyzing the esterification reaction with organozirconium compounds, diphenyl esters can be prepared which have good color properties.

The following example illustrates the best mode now contemplated for carrying out the invention.

EXAMPLE 150 g isophthalic acid, 50 g terephthalic acid, 2.7 g zirconium tetra-n-propoxide (0.65 mol % based on acids) are added under nitrogen pressure to a stainless steel, stirred, 2-liter, cylindrical vessel. The vessel is closed and 100 g of phenol is then pumped into the vessel and the mixture heated to 100° C. with stirring. The temperature is increased to 266° C. while phenol is continuously pumped in to provide a total of 560 g phenol. The vapor outlet is unblocked and liquid phenol is continuously pumped in and distilled off, with water, at balanced rates to maintain a constant liquid volume in the reactor. Reactor pressure, usually about 40 to 80 psi, is set to accommodate temperature and distillation rate. The phenol-water vapor is sent to a condenser-receiver and the reaction is over 97% complete at the end of 8 hours as evidenced by the decrease in the acidity of the reaction mixture. Excess phenol is then flashed off at 10–100 mm Hg. K2CO3 in slight excess over the total acid was added to the crude diester (which was gray colored) and the diester was distilled through a short Vigreaux column at 1 mm Hg - boiling range 235°–245° C. The molten diester had an APHA color of 50.

The same mode of operation was carried out with titanium tetra-n-butoxide at conditions of equivalent kinetics. However, with the titanate, only 0.13 mol % and 240° C. were required to reach approximately 97% conversion in 8 hrs. The crude color, though, was reddish brown and the distilled, molten diester had an APHA color of 300.

What is claimed:

1. In a method for reacting a phenol with an aromatic carboxylic acid under conditions of esterification to form the phenolic ester thereof, the improvement of carrying out the esterification reaction in the presence of an effective amount of a zirconium alkoxide catalyst, and thereafter recovering a phenolic ester having improved color properties.

2. The method of claim 1 wherein the carboxylic acid is an aromatic dicarboxylic acid and the catalyst is present in an amount ranging from about 0.01 to 3.0 mol % based on the acid.

3. The method of claim 2 wherein the zirconium alkoxide catalyst contains 1 to 4 carbon atoms in the alkyl group.

4. The method of claim 3 wherein the catalyst is zirconium tetra-n-propoxide.

5. The method of claim 3 wherein the dicarboxylic acid is isophthalic acid, terephthalic acid, or mixtures thereof.

* * * * *